United States Patent [19]

Anis

[11] 4,143,427
[45] Mar. 13, 1979

[54] METHOD AND APPARATUS FOR ACCOMPLISHING APHAKIC CORRECTION

[76] Inventor: Aziz Y. Anis, 7531 N. Hampton, Lincoln, Nebr. 68506

[21] Appl. No.: 805,265

[22] Filed: Jun. 10, 1977

[51] Int. Cl.² .................... A61F 1/16; A61F 9/00; A61B 17/28
[52] U.S. Cl. .................................. 3/13; 128/321; 128/335; 128/337; 85/49
[58] Field of Search .............. 3/13, 1; 128/337, 335, 128/321, 303 R; 85/49

[56] References Cited

U.S. PATENT DOCUMENTS

| | | | |
|---|---|---|---|
| 2,667,645 | 2/1954 | Moulton | 3/13 |
| 3,098,232 | 7/1963 | Brown | 85/49 |
| 3,203,220 | 8/1965 | Kaepernik | 128/335 UX |
| 3,378,010 | 4/1968 | Codling et al. | 128/337 X |
| 3,906,551 | 9/1975 | Otter | 3/13 |
| 3,994,027 | 11/1976 | Jensen et al. | 3/13 |

FOREIGN PATENT DOCUMENTS 178032  6/1966  U.S.S.R. .................. 128/337

*Primary Examiner*—Ronald L. Frinks
*Attorney, Agent, or Firm*—Henderson & Sturm

[57] ABSTRACT

Method and apparatus are disclosed for surgical accomplishment or aphakic correction. After intracapsular cataract extraction has been successfully completed the artificial lens, held securely in the Binkhorst implant forceps, is introduced into the anterior chamber. The three posterior loops of the implant are then inserted behind the iris through the pupil with the bend of the anterior loop in front at the 12 o'clock position across the iridectomy. The posterior loop is held and stabilized through the iridectomy with a loop forceps while a specially designed micro staple positioned in a holder and locked therein is placed over the anterior loop of the implant and pressed until the ends of the micro staple clear the posterior loop. The blades of the micro staple holder are pressed firmly to close the micro staple. The forceps and micro staple holder are then removed. The anterior chamber is then formed with an air bubble and the section closed with 9.0 monofilament nylon sutures, the air is then removed and replaced with balanced salt solution. The procedure is then completed.

11 Claims, 11 Drawing Figures

METHOD AND APPARATUS FOR ACCOMPLISHING APHAKIC CORRECTION

BACKGROUND OF THE INVENTION

This invention is directed generally to aphakic correction, and particularly to method and apparatus for surgical accomplishment of aphakic correction.

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are innumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view inasmuch as it cannot properly refract incident light rays. Aphakic correction may be accomplished in three ways:
1. Thick eye glasses worn in front of the eye;
2. Contact lenses worn on the eye; or
3. Artificial intraocular lens implant within the eye. It is this latter procedure with which the instant invention is concerned.

The structure and procedure of installing an intraocular lens is very critical because the elements which make up the eye are extremely sensitive and subject to irrepairable damage. Numerous experimental lens designs and surgical techniques for implantation have been tried through the years with varying degrees of success. Usually, the prior art procedures have been abandoned because the lens design and surgical techniques have proved to cause corneal damage and/or other manifestations of intraocular irritation. For example, in the late 1940's and early 1950's, H. Ridely conducted clinical experiments with an artifical intraocular lens which included a lens portion having foot-like projections extending radially away therefrom. This device was placed in the posterior chamber with the feet extending between the ciliary processes and the base of the iris. The lens proved positionally unstable because there was no means for fixing the location of the implant relative to the iris, and resulted in unsatisfactory amounts of irritation.

The device and procedure disclosed in U.S. Pat. No. 3,906,551 purports to solve the positional integrity problem; however, the implant must be sutured into position. Such suturing in a confined area is, at best, extremely difficult and potentially damaging to the eye, and is very often unsatisfactorily accomplished.

U.S. Pat. No. 3,866,249 discloses a posteriorly positioned prosthetic lens which has a multiplicity of forwardly projecting prongs. During surgical implantation, the prongs are extended through the iris to anchor the lens in position. While this arrangement certainly maintains positional integrity, the great number of prongs extending through and over the iris promote undesirable irritational characteristics, and the numerous fixation points have a tendency to distort the iris by pulling on it in numerous directions.

BRIEF SUMMARY OF THE INVENTION

It is an object of this invention to provide efficient method and apparatus for surgical accomplishment of aphakic correction.

Another object of this invention is to provide method and apparatus for surgical accomplishment of aphakic correction which minimize post-operative recovery times.

Another object of this invention is to provide a novel micro staple for affixing an intraocular lens implant in an aphakic eye.

Another object of this invention is to provide a micro staple which is durable of construction, inexpensive of manufacture and extremely effective in use.

These, and other objects are obtained, according to the instant invention, by providing method and apparatus for surgical accomplishment of aphakic correction. After intracapsular cataract extraction has been successfully completed the artificial lens, held securely in the Binkhorst implant forceps, is introduced into the anterior chamber. The three posterior loops of the implant are then inserted behind the iris through the pupil with the bend of the anterior loop in front at the 12 o'clock position across the iridectomy. The posterior loop is held and stabilized through the iridectomy with a loop forceps while a specially designed micro staple positioned in a holder and locked therein is placed over the anterior loop of the implant and pressed until the ends of the micro staple clear the posterior loop. The blades of the micro staple holder are pressed firmly to close the micro staple. The forceps and micro staple holder are then removed. The anterior chamber is then formed with an air bubble and the section closed with 9.0 monofilament nylon sutures, the air is then removed and replaced with balanced salt solution. The procedure is then completed.

BRIEF DESCRIPTION OF THE DRAWINGS

For a better understanding of the invention as well as other objects and further features thereof, reference is made to the following detailed disclosure of the invention taken in conjunction with the accompanying drawings wherein.

DESCRIPTION OF THE PREFERRED EMBODIMENTS

Figure 1:
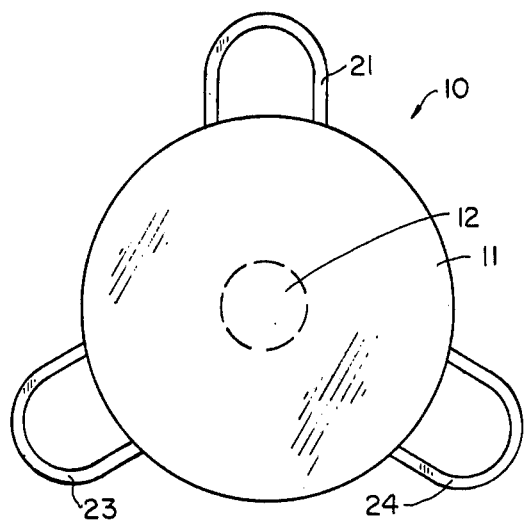
FIG. 1 is a partially schematic top plan view of a lens implant to be used with the instant invention.
Figure 2:
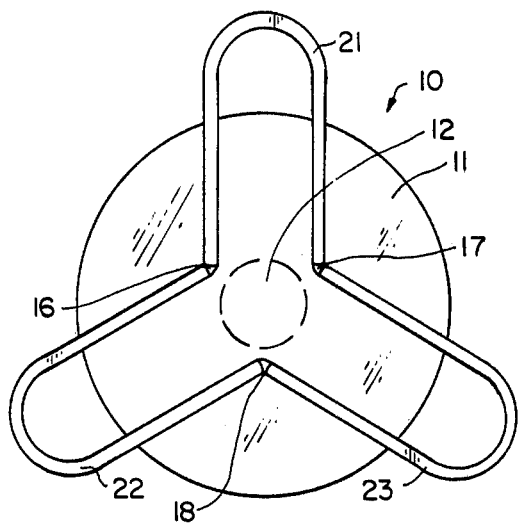
FIG. 2 is a partially schematic, bottom plan view of the implant of FIG. 1.
Figure 3:
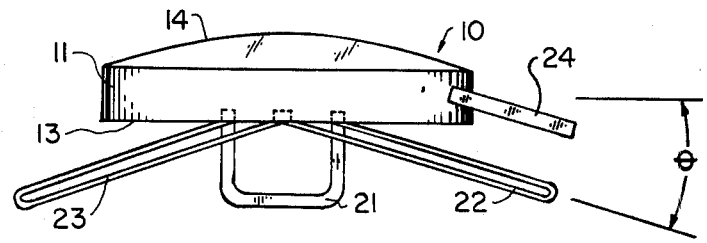
FIG. 3 is a partially schematic, side elevational view of the implant of FIGS. 1 and 2 showing the relationship among the various loops.

Referring now to FIGS. 1-3, the intraocular lens implant 10 for use with the instant invention is seen to include a substantially light transparent lens 11 with a central optical zone 12. The lens 11 may be of any suitable diameter, but generally falls somewhere in the range of about 5mm. (millimeters) to about 6mm. It should be realized that the parameters and ranges given herein are merely exemplary and that actual optical and surgical variables are subjectively determined by the opthalmologic surgeon in charge of the patient. The lens 11 may be made of any suitable material which may be made to exhibit the proper optical characteristics, and which is biologically inert. "Biologically inert" is a term used in the art to describe materials which are not susceptible to being absorbed by body fluids and which are capable of being tolerated by the human body when implanted. The most suitable material known for such lens implants is substantially polymethylmethacrylate, a compound commonly used in contact lens manufacture. Other suitable materials include quartz, ophthalmic glass and polymeric materials.

Implant 10 is described in more detail in co-pending application Ser. No. 805,390; filed simultaneously herewith in the name of the same inventor as the instant application and entitled "Intraocular Lens Implant." Lens 11 may, of course, have generally any suitable cross-sectional configuration; however, it has been found that a flat rear surface 13 more easily accommodates an expanding and contracting pupil. The front surface 14 may be modified to provide the desired optical characteristics.

Three affixment points 16, 17 and 18 are positioned 120° apart around the center of the lens at the edge of the optical zone 12. U-shaped loops 21, 22 and 23 are positioned relative to each other such that the adjacent free ends of the adjacent loops are affixed to the lens 11 at the same affixment point. An additional loop 24 is affixed to the edge of lens 11, see FIG. 3, and projects laterally away therefrom substantially in the plane of loop 22. Loop 24 is in substantial vertical alignment with loop 22, so that the top and bottom plan views show only one of these loops. The loops can be made of any suitable material that is biologically inert and can be formed or drawn to a diameter of from about 0.10mm. to about 0.20mm. For example, two polyamide synthetic fibers have been found particularly useful, one is identified as Prolene, a trade name of Ethicon Corporation, and the other is Supramid, a trade name of Jackson Company.

THe three-point connection described immediately above is highly advantageous in aphakia correction. The number of elements which make up the implant is greatly reduced over the prior art, and thus potential irritation is minimized as are the possibilities of injury due to structure breakage. With the U-shaped holding elements affixed adjacent the optical zone, the iris is free to expand and contract to its full and natural limits without substantial contact with the implant.

Figure 4A:
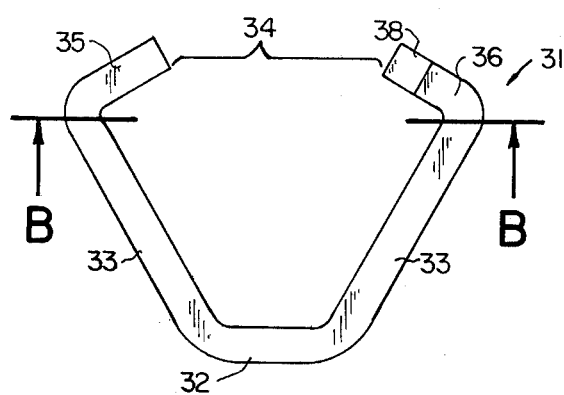
FIG. 4A is a partially schematic view of the micro staple of the instant invention.
Figure 4B:
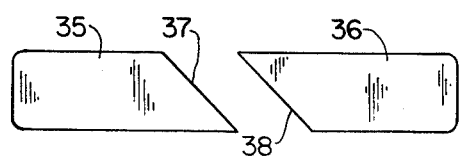
FIG. 4B is a partial sectional view of the micro staple taken along line B-B of FIG. 4A.

FIG. 4A shows a micro staple 31 which makes up part of the instant invention. The staple is made of a biologically, inert, elongate material, such as titanium, of about 0.15mm diameter, with a base 32 of about 0.3mm, diverging arms 33 of about 0.75mm and converging legs 35 and 36 of about 0.15mm and a gap 34 of about 0.44mm forming a symmetrical open-sided polygon. Micro staple 31 is uniquely designed to be efficiently inserted through various tissue of the eye for permanent or temporary affixment without interference with, or impairment of, the normal eye functions. Although in FIG. 4 the microstaple 31 is depicted to be generally rectangular in cross section it can also be substantially circular without departing from the invention. The micro staple closes neatly into substantially a rectangular configuration with a minimum of free edges. As best seen in FIG. 4B, the ends 37 and 38, respectively, of legs 35 and 36 are tapered to form cutting edges for easier implantation and to cooperatively engage each other in a mating connection wherein the outer surfaces of the legs are generally in longitudinal alignment for a neat, safe fixture.

Figure 5:
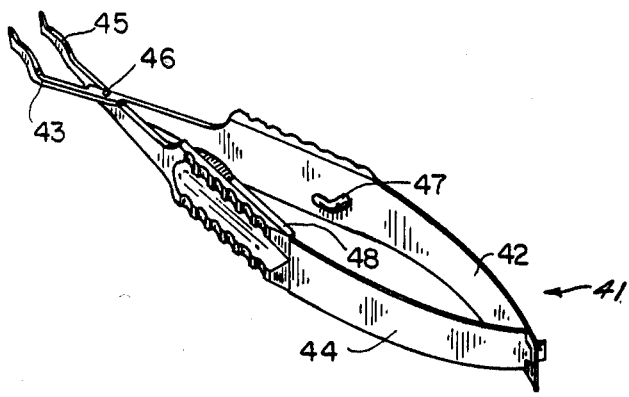
FIG. 5 is a schematic view of a micro staple holder useful with the method of the instant invention.

FIG. 5 shows the micro staple holder to be used with the instant invention. Micro staple holder 41 comprises two resilient legs 42 and 44, terminating in pincer ends 43 and 45, respectively. A pivot point 46 causes the pincer ends 43 and 45 to approach each other as the two legs 42 and 44 are pressed together. A known lock and release mechanism comprising a latch 47 and resilient catch 48 are disposed interiorly of the two resilient leg members. The lock is designed to catch as the two legs are brought together. In the catch position the pincer ends 43 and 45 are spaced closely together to hold the micro staple 31 of FIG. 4 in fixed position yet without closing gap 34. To release the "catch" the legs 42 and 44 are pressed closer together to cause the pincers 43 and 45 to move closer together and thus close the gap 34 in micro staple 31.

Figure 6:
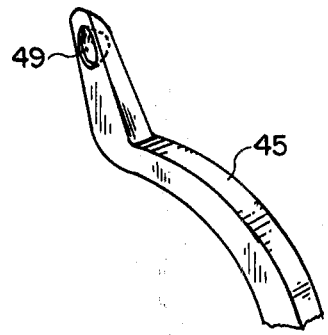
FIG. 6 is a perspective partial view of the blade tip of the micro staple holder of FIG. 5.

FIG. 6 is a close up of the pincer 45 and shows that it contains a groove 49 in the end thereof which receives the exterior elbow of the micro staple 31. Pincer 43 has a like indent therein so that the two indents oppose each other and grip the micro staple in a stable attitude.

Figure 7A:
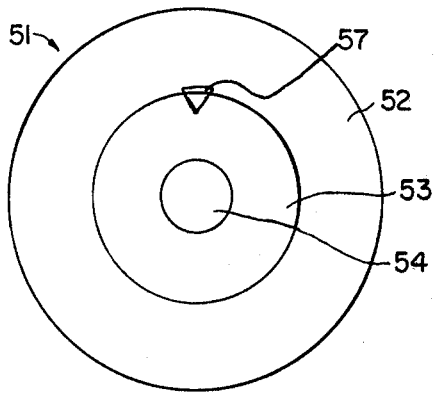
FIG. 7A is a schematic front plan view of an eye.
Figure 7B:
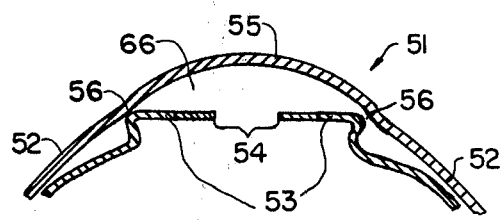
FIG. 7B is a schematic side sectional view of the eye of FIG. 7A.

FIGS. 7A and 7B are partially schematic front plan and side sectional views of an eye 51 which serve as a brief introduction to the operational methods of the instant invention. The portion of the eye shown comprises a conjuntiva 52 and an iris 53 which defines, interiorly, a pupil 54 behind which the natural lens would be located. The sclera 52 merges into the cornea 55 in a peripheral transition line 56 known as the corneoscleral limbus, which is roughly in vertical alignment with the outer edge of the iris as shown in these figures.

To remove the cataract, a limbal incision of between about 160° and 180° is made in the upper limbus. The corneal flap is elevated to provide access to the anterior chamber. A peripheral iridectomy 57 is made at the 12 o'clock position and the cateract is removed through the pupil.

Figure 8:
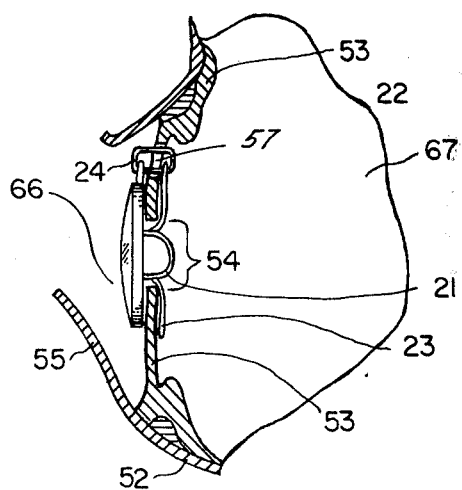
FIG. 8 is a sectional view showing the micro staple in proper position holding the implant relative to the iris.
Figure 9:
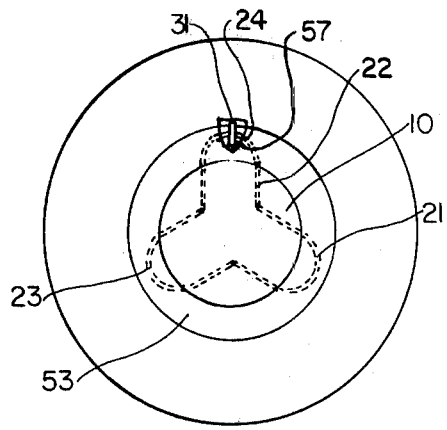
FIG. 9 is a perspective view of an eye showing the micro staple of the instant invention in proper position relative to the iridectomy.

Referring now to FIG. 8, the position and affixment of the lens implant 10 within the aphakic eye can be seen. The aphakic eye comprises a transparent cornea 55 which merges into the opaque sclera 52. The iris 53 comprises a muscular diaphragm-like element capable of expansion and contraction to control the amount of light passed therethrough. The iris divides the internal chamber of the eye into two chambers, the anterior chamber 66 and the posterior chamber 67. The natural crystalline lens of the eye would be located in the posterior chamber 67 adjacent to pupil 54.

As can be seen clearly in this figure, the lens 11 is positioned within the anterior chamber 66 in contact with the forward portion of iris 53. The rear loops 21, 22 and 23 extend through the pupil and behind the iris 53. The loops alone will keep the lens 11 within the pupil, but will not guarantee total positional integrity. The loop 24 extends along the forward portion of the iris, substantially opposite loop 22, at the 12 o'clock position.

The procedure for inserting the lens into the aphakic eye is very critical and difficult, and requires the skill of a highly trained surgeon. After removal of the cataract, as explained briefly above in relation to FIGS. 7A and 7B, the implant 10 is grapsed by a well known Binkhorst forceps and introduced into the anterior chamber 6. The three posterior loops 21-23 of the implant are then inserted behind the iris through the pupil with the bend of the anterior loop 24 in front at the 12 o'clock position across the iridectomy 57. The posterior loop is held and stabilized through the iridectomy with a forceps. The forceps are specially designed tweezers having a groove cut in each of the opposing pincers substantially the same size as the diameter of the loop material. A micro staple 31, positioned in a holder, like 41, and locked therein is placed over the anterior loop 24 of the implant and pressed until the ends of the micro staple clear the posterior loop 22. The blades 42 and 44 of the micro staple holder are then pressed firmly to close the micro staple. The forceps and micro staple holder are then removed. The anterior chamber is then formed with an air bubble and the corneoscleral incision closed with suitable sutures, such as, for example, 9.0 monofilament nylon. The air is then removed and replaced with a balanced salt solution. The procedure is now completed.

It will be understood that various changes in the details, materials, steps and arrangements of parts, which have herein been described and illustrated in order to explain the nature of the invention, will occur to and may be made by those skilled in the art upon a reading of the disclosure within the principles and scope of the invention.

I claim:

1. A micro staple for use in aphakic correction comprising:
   an elongate member of biologically inert material, said elongate member formed into a symmetrical open-sided polygon having a base connected to two diverging arms which terminate, respectively, in two converging legs; and
   said two converging legs have angularly shaped ends which when pressed together form a mating connection with the outer surfaces of said legs in longitudinal alignment.

2. The micro staple of claim 1 wherein said base is about 0.3mm in length, said two diverging arms are each about 0.75mm in length and said two converging legs are each about 0.15mm in length.

3. The micro staple of claim 2 wherein the open side of said polygon is about 0.44mm.

4. The micro staple of claim 3 wherein said elongate member is substantially circular in cross section with a diameter of about 0.15 mm.

5. The micro staple of claim 4 wherein said elongate member is made of titanium.

6. A micro staple for use in aphakic correction comprising:
   an elongate member of a biologically inert material, said elongate member formed into a symmetrical open-sided polygon having a base connected to two substantially identical in length diverging arms which terminate, respectively, in two converging legs, said legs being of substantially equal length and equal to approximately one-half the length of said base, and when said member is closed with the ends of said legs pressed together in a mating connection the outer surfaces of said legs are in longitudinal alignment.

7. The micro staple of claim 6 wherein said base is about 0.3mm in length, said two diverging arms are each about 0.75 mm in length and said two converging legs are each about 0.15mm in length.

8. The micro staple of claim 7 wherein the open side of said polygon is about 0.44mm and said elongate member is substantially circular in cross section with diameter of about 0.15mm.

9. The micro staple of claim 8, wherein the said two diverging arms have angularly-shaped ends which, when pressed together, mate to form a substantially cylindrical connection.

10. In a method of aphakic correction wherein the cataract has been removed through a corneoscleral incision and a peripheral iris iridectomy has been made, the improvement comprising the steps of:
   (a) providing a biologically inert artificial intraocular lens implant comprising a lens having a front face, a substantially flat rear face and an outer peripheral edge; said rear face of said lens further including first, second and third holes therein extending partway through said lens toward said front face, said holes being equally spaced from the center of the lens and about 120° apart; first, second and third U-shaped holding members each said holding member including a looped portion between first and second free ends, the said free ends of said holding members positioned in and fixedly secured to said first, second and third holes such that two of said free ends are in each hole, one from each adjacent holding member; said outer edge of said lens further including fourth and fifth holes therein extending partway into said lens; and a fourth U-shaped holding member including a looped portion between first and second free ends, the said free ends of said fourth holding member positioned in and fixedly secured to said fourth and fifth holes, respectively, said fourth and fifth holes being positioned relative to said first and second holes such that said fourth U-shaped holding member is in substantially the same vertical plane as the U-shaped holding member having its first free end in said first hole and its second free end in said second hole;
   (b) gripping the lens implant with a forcep and inserting the lens implant through the incision in such a manner that the first, second and third U-shaped holding members pass through the pupil to contact the rear portion of the iris and the fourth U-shaped holding member is at the 12 o'clock position in contact with the front portion of the iris across the iridectomy;
   (c) providing a micro staple comprising an elongate member of a biologically inert material, said elongate member formed into a symmetrical open-sided polygon having a base connected to two diverging arms which terminate, respectively, in two converging legs;
   (d) stabilizing the first U-shaped holding member through the iridectomy with the loop forceps;

(e) placing said micro staple in a staple holder;
(f) pressing said micro staple through the iridectomy such that one leg thereof passes through said fourth U-shaped holding member and one of said first, second, or third U-shaped holding members;
(g) closing said micro staple to hold said lens implant in position;
(h) removing said forcep and said staple holder through said incision;
(i) pulling the edges of said incision together; and
(j) suturing the incision closed.

11. The method of claim 10 wherein the base of said micro staple is about 0.3mm in length, said two diverging arms are each about 0.75mm in length and said two converging legs are each about 0.15mm in length.

* * * * *